(12) United States Patent
Oakland

(10) Patent No.: US 8,968,255 B2
(45) Date of Patent: Mar. 3, 2015

(54) DRUG DELIVERY WITH AN IMPROVED PISTON ROD

(75) Inventor: Philip Oakland, Stockport (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 503 days.

(21) Appl. No.: 13/258,575

(22) PCT Filed: Mar. 26, 2010

(86) PCT No.: PCT/EP2010/053968
§ 371 (c)(1),
(2), (4) Date: Dec. 6, 2011

(87) PCT Pub. No.: WO2010/112409
PCT Pub. Date: Oct. 7, 2010

(65) Prior Publication Data
US 2012/0109074 A1    May 3, 2012

Related U.S. Application Data

(60) Provisional application No. 61/169,849, filed on Apr. 16, 2009.

(30) Foreign Application Priority Data

Mar. 30, 2009  (EP) .................................... 09004570

(51) Int. Cl.
*A61M 5/315* (2006.01)
*A61M 5/24* (2006.01)

(52) U.S. Cl.
CPC ....... *A61M 5/31585* (2013.01); *A61M 5/31551* (2013.01); *A61M 5/31558* (2013.01); *A61M 5/24* (2013.01); *A61M 5/31511* (2013.01); *A61M 5/31575* (2013.01); *A61M 2005/2407* (2013.01)

USPC ............................ 604/211; 604/207; 604/208

(58) Field of Classification Search
CPC .............. A61M 5/31551; A61M 5/24; A61M 5/31593; A61M 5/3158; A61M 5/31561; F16B 31/021; F16B 41/005; F16B 35/045; F16B 31/02; F16B 35/041; F16B 35/06; F16B 33/06; F16B 35/044; F16B 33/006; F16B 5/02; E21B 19/16; E05B 15/10; E05B 17/08; E05B 17/2003; E05B 17/0045; E05B 17/007; B25B 13/48; B25B 13/481; B25B 13/5091; B25B 17/00
USPC .............. 604/211, 207, 208, 228, 232; 411/5, 411/378; 292/2; 81/52
See application file for complete search history.

(56) References Cited

U.S. PATENT DOCUMENTS 6,004,297 A    12/1999 Steenfeldt-Jensen et al.
(Continued)

FOREIGN PATENT DOCUMENTS

EP    1923085 A1    5/2008
(Continued)

OTHER PUBLICATIONS

European Search Report for EP Patent App. No. 09004570, dated Sep. 10, 2009.
(Continued)

*Primary Examiner* — Bhisma Mehta
*Assistant Examiner* — William Frehe
(74) *Attorney, Agent, or Firm* — McDonnell Boehnen Hulbert & Berghoff LLP

(57) ABSTRACT

An improved drug delivery device is provided having a piston rod that incorporates on its proximal end at least one guidepost that is configured for transmitting axial and rotational forces from a drive mechanism. The device comprises a drug delivery device housing and a medicament contained in the drug delivery device housing.

7 Claims, 2 Drawing Sheets

(56) References Cited

U.S. PATENT DOCUMENTS

| | | | |
|---|---|---|---|
| 6,936,032 B1 * | 8/2005 | Bush et al. | 604/187 |
| 2003/0004467 A1 | 1/2003 | Musick et al. | |
| 2006/0206057 A1 | 9/2006 | DeRuntz et al. | |

FOREIGN PATENT DOCUMENTS

| | | | | |
|---|---|---|---|---|
| WO | 0110484 | A1 | 2/2001 | |
| WO | 2004078241 | A1 | 9/2004 | |
| WO | WO2007006662 | * | 1/2007 | 604/208 |
| WO | WO 2007006662 A1 | * | 1/2007 | 604/207 |

OTHER PUBLICATIONS

International Search Report for PCT Patent App. No. PCT/EP2010/053968, completed Apr. 27, 2010.

* cited by examiner

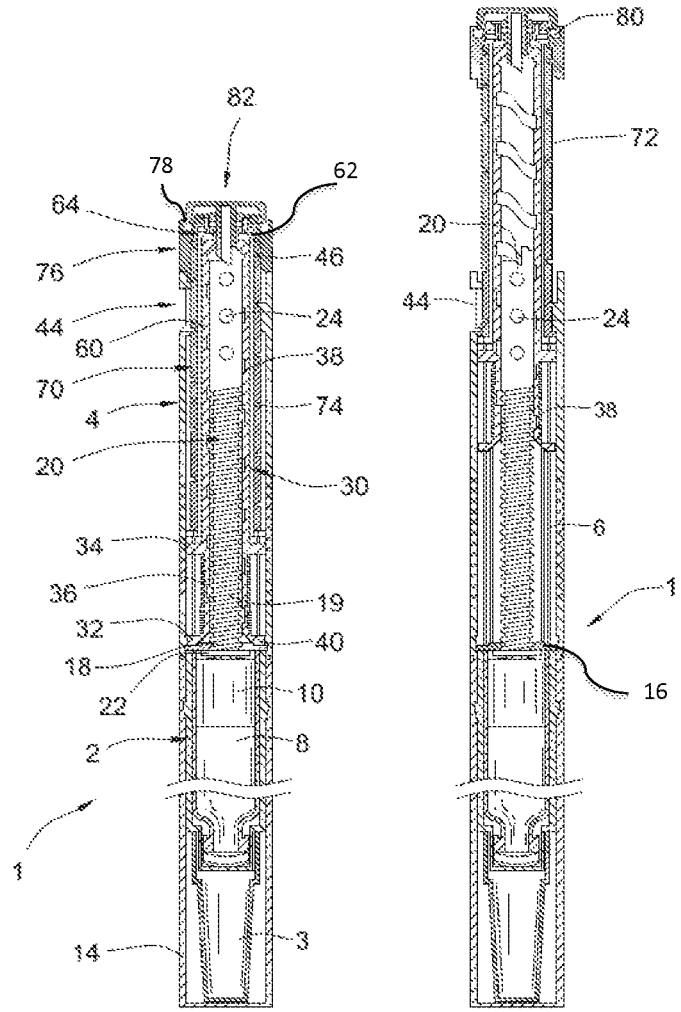

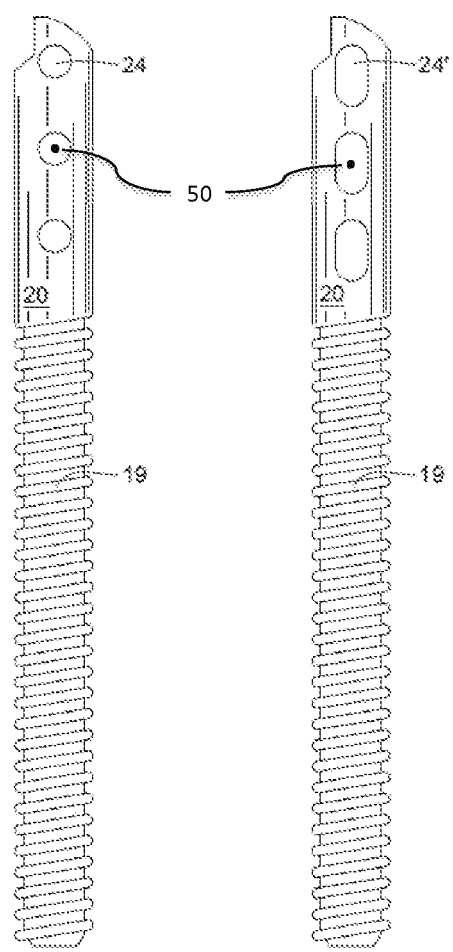

DRUG DELIVERY WITH AN IMPROVED PISTON ROD

CROSS REFERENCE TO RELATED APPLICATIONS

The present application is a U.S. National Phase Application pursuant to 35 U.S.C. §371 of International Application No. PCT/EP2010/053968 filed Mar. 26, 2010, which claims priority to European Patent Application No. 09004570.9 filed on Mar. 30, 2009 and U.S. Provisional Patent Application No. 61/169,849 filed on Apr. 16, 2009. The entire disclosure contents of these applications are herewith incorporated by reference into the present application.

FIELD OF THE INVENTION

The present invention relates to pen-type injectors, that is to injectors of the kind that provide for administration by injection of medicinal products from a multi-dose cartridge. In particular, the present invention relates to such injectors where an improved piston rod having guideposts manages high dispensing loads transmitted by a drive member or mechanism.

BACKGROUND

Pen type drug delivery devices have application where regular injection by persons without formal medical training occurs. This is increasingly common among patients having diabetes where self-treatment enables such patients to conduct effective management of their disease.

Diabetes has been shown to cause certain problems. For example, people with diabetes can get high blood pressure, kidney disease, nerve damage, heart disease, and even in certain circumstances blindness. The damage caused by these problems may occur in patients whose blood sugar has been out of control for years. Keeping blood sugar under control, by way of effective insulin administration, is one method that can help prevent this damage from occurring.

In addition, people with diabetes can go into "diabetic coma" if their blood sugar is too high. They can also develop blood sugar that is too low (i.e, hypoglycemia) if they don't get enough food, or they exercise too much without adjusting insulin or food. Both diabetic coma and hypoglycemia can be very serious, and even fatal, if not treated quickly. Closely watching blood sugar, being aware of the early signs and symptoms of blood sugar that is too high or too low, and treating those conditions early can prevent these problems from becoming too serious.

Pen type drug delivery devices have been designed and developed to help patients suffering from diabetes so as to prevent such problems from occurring. The circumstances identified above highlight a number of design considerations and criteria for drug delivery devices, especially those that may be used to treat diabetes. As just one example, one requirement is that the drug delivery device must be robust in construction. The drug delivery device must also be easy to use both in terms of the drug delivery device manipulation and understanding of the device's operation. Diabetics have to inject themselves repeatedly with insulin solution and the volume of insulin to be injected may vary from patient to patient and even from injection to injection. For at least this reason, certain diabetics may require drug delivery devices that allow the patient to inject successive measured dosages of the same or perhaps different preset volumes of insulin solution accurately and with minimum dexterity challenges. This presents a further design challenge since, in the case of certain diabetics, users may have impaired vision and/or may be physically infirm with limited dexterity.

Pen-type injectors are well known and typically each use some form of a piston rod to axially drive or push a rubber stopper in a cartridge towards the distal end of the injector to dispense medicament from the cartridge through an attached needle. Such injectors have application where regular injection by persons without formal medical training occurs. This is increasingly common amongst those having diabetes where self-treatment enables such persons to conduct effective management of their diabetes.

These circumstances set a number of requirements for pen-type injectors of this kind. The injector must be robust in construction, yet easy to use both in terms of the manipulation of the parts and understanding by a user of its operation. In the case of those with diabetes, many users will be physically infirm and may also have impaired vision. Where the injector is to be disposable rather than reusable, the injector should be inexpensive to manufacture and easy to dispose of (preferably being suitable for recycling).

One problem frequently encountered when using these pen-type is high dispensing loads that can be caused by a blocked or clogged needle, or where the user forgets to attach a needle, or where the user applies excessive force during the injection, typically by injecting too fast. A drive member or sleeve ultimately transmits these high dispensing loads to the proximal end of the piston rod, which in turn transmits the forces to the piston or bung in a cartridge of medicament. Such loads manifest themselves as rotational and/or axial forces and can cause jamming of the device and even shearing or breaking of the piston rod.

OBJECT OF THE INVENTION

It is therefore an object of the invention to provide an improved piston rod and an improved drug delivery device which has a reduced risk of jamming of the device or destroying the piston rod.

SUMMARY

Our invention solves these problems by using guideposts, pins, pegs, followers or the like structures that protrude outwardly from the proximal end of a piston rod and are designed to interact with a corresponding groove in a drive sleeve to transmit forces from a drive mechanism to the piston rod. These and other advantages will become evident from the following more detailed description of the invention.

According to an exemplary embodiment, a drug delivery device comprises a device housing and a medicament contained in the device housing. A drive mechanism is positioned in the housing for transmitting axial and/or rotational force to a piston rod comprising an elongated member having a distal end and a proximal end. The shape of rod is not critical to our invention, likewise the material of construction is not important, except that the rod must be able to drive or push a rubber stopper or bung in a cartridge of medicament towards the distal end during injection of a set dose. Preferably, the proximal end of the piston rod should be made of low friction type plastics so that the transfer of forces from the drive member is not dissipated by friction losses.

A preferred shape of the improved piston rod of our invention is generally circular and is fabricated from a polymeric material through molding or machining. A metallic material may also be used to fabricate all or part of the piston rod. The proximal end of the piston rod interacts with a drive sleeve and has at least one guidepost extending outwardly from the elongated member and is configured to engage a cooperating or corresponding groove in a drive member and for transmitting axial or rotational forces from the drive member. When multiple guideposts are used, the orientation of the posts relative to each other can be any design that facilitates the transfer of force (axial and/or rotational) from the drive member to the piston rod. Non-axial alignment of the posts may provide strength benefits. Preferably, the guideposts fall in a path that corresponds to one or more grooves or slots on or in the drive member.

In another embodiment the invention comprises at least two sets of two or more guideposts, where the guideposts are in axial alignment with each other. These posts can be any geometric shape or a mix of geometric shapes. Preferably, the posts are circular or oblong in shape and configured for transmitting axial and/or rotational forces from a drive mechanism having at least one drive member having a corresponding internal groove with a pitch P. These posts, pegs or pins provide a uniform contact angle with respect to the groove in the drive member to reduce friction and the risk of jamming during injection. Another benefit is that the guideposts are simpler to manufacture as compared to a thread, thus reducing tooling costs and are easier to control and inspect the quality.

In a preferred embodiment, there are two sets of guideposts located on opposing sides of the proximal end of the rod, where each set contains at least three guide-posts circular in shape. In some cases it might be advantageous to include threads on the distal end of the piston rod. When a threaded distal end is used, it is preferred that these threads on the distal end of the piston rod are oppositely disposed to the groove of the drive sleeve.

A drive mechanism is connected either directly or indirectly with the proximal end of the piston rod and in a preferred embodiment is directly connected to the guideposts through a groove or grooves of corresponding dimension located on or in a drive sleeve member. Preferably the groove(s) in the drive member are a square or buttress type design.

In an alternative arrangement, a pen type drug delivery device comprises a device housing having a distal end for mounting a needle assembly and a proximal end comprising a dose dial grip. A cartridge is contained in the housing, which contains a medication and a stopper. The improved piston rod of our invention acts upon the stopper to expel medication from the cartridge during dose delivery. Preferably, the proximal end of the piston rod and/or the groove(s) in the drive member are made using materials exhibiting low friction qualities.

These as well as other advantages of various aspects of Applicants' proposed drug delivery device will become apparent to those of ordinary skill in the art by reading the following detailed description, with appropriate reference to the accompanying drawings.

The term "medication", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2, H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the aforementioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane such as hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Exemplary embodiments are described herein with reference to the drawings, in which:

FIG. 1 illustrates a sectional view of a first embodiment of the drug delivery device in accordance with the one arrangement of the device in a first, cartridge full, position;

FIG. 2 illustrates a sectional view of the drug delivery device of FIG. 1 in a second, maximum first dose dialed, position;

FIG. 3 shows a perspective view of one embodiment of a piston rod according to one embodiment of the invention having circular guide posts; and FIG. 4 shows a perspective view of another embodiment of a piston rod according to another embodiment of the invention having oblong shaped guideposts.

DETAILED DESCRIPTION

Referring first to FIGS. 1 and 2, there is shown a drug delivery device 1 in accordance with the one arrangement in a plurality of operating positions: for dose setting and for dose administration or injection. The drug delivery device 1 comprises a housing having a first cartridge retaining part 2, and second main (exterior) housing part 4. A first end of the cartridge retaining means 2 and a second end of the main housing 4 are secured together by retaining features. In this illustrated arrangement, the cartridge retaining means 2 is secured within the second end of the main housing 4.

A cartridge 8 from which a number of doses of a medicinal product may be dispensed is provided in the cartridge retaining part 2. Preferably, the cartridge 8 contains a type of medicament that must be administered often, such as once or more times a day. One such medicament is insulin. A piston 10 is retained in a first end of the cartridge 8. A removable cap 3 is releasably retained over a second end of the cartridge retaining part 2.

The dose setting mechanism of the drug delivery device illustrated in FIGS. 1-2 may be utilized as either a disposable or reusable drug delivery device. Where the drug delivery device comprises a disposable drug delivery device, the cartridge cannot be removed from the device without destroying the device. Alternatively, where the drug delivery device comprises a reusable drug delivery device, the cartridge is removable and may be removed from the device without destroying the device. In the drug delivery device 1 illustrated in FIGS. 1-2, this drug delivery device is illustrated as a disposable drug delivery. However, those of ordinary skill in the art will recognize that the dose setting mechanism could also be used on reusable drug delivery devices as well.

In use, the removable cap 3 can be replaced by a user with a suitable needle unit (not shown). Such needle unit may be screwed onto a distal end of the housing or alternatively may be snapped onto this distal end. A replaceable cap 14 is used to cover the cartridge retaining part 2 extending from the main housing 4. Preferably, the outer dimensions of the replaceable cap 14 are similar or identical to the outer dimensions of the main housing 4 so as to provide an impression of a unitary whole when the replaceable cap 14 is in position covering the cartridge retaining part 2.

Referring also to FIGS. 3 and 4, a first helical groove 19 extends from a first end of a piston rod 20. In one arrangement, the piston rod 20 is of generally circular in cross section however other arrangements may also be used. The first end of the piston rod 20 (the distal end of the piston rod 20) extends through the threaded opening 18 in the body 4. A pressure foot 22 is located at the first end or distal end of the piston rod 20. The pressure foot 22 is disposed to abut a second end of the cartridge piston 10. On the second end of piston rod 20 are guideposts 24, shown in FIGS. 1 & 2 for that embodiment as circular knobs or pins (also see FIG. 3), which extend radially outward along a single longitudinal axis 50 from the proximal end of the piston rod 20. In another embodiment shown in FIG. 4, guideposts 24 are oblong in shape. Regardless of the shape of the guideposts, they are used to communicate with and transmit axial and/or rotational forces from drive sleeve 30 to piston rod 20 and eventually to cartridge piston 10.

The guideposts or guide ribs can be designed in any geometric shape or combination of shapes. Preferred shapes are circular guide posts 24 (FIG. 3) or oblong guide posts 24' (FIG. 4). The upper most post may be a complete form as shown in the drawings or may be a partial or truncated shape form, for example a half circle. The geometry of these guideposts is selected to withstand high dispensing loads. Because the posts or ribs 24, 24' contact the drive sleeve at single defined points this will reduce the likelihood of jamming of the drive mechanism that can be caused by mismatched thread forms. The pitch of the guide ribs 24, 24' is easy to specify and monitor during manufacturing and critical dimensions can be measured point-to-point.

A drive sleeve 30 extends about the piston rod 20. The drive sleeve 30 is generally cylindrical. The drive sleeve 30 is provided at a first end with a first radially extending flange 32. A second radially extending flange 34 is provided spaced a distance along the drive sleeve 30 from the first flange 32. An intermediate helical groove 36 is provided on an outer part of the drive sleeve 30 extending between the first flange 32 and the second flange 34. A helical groove 38 extends along the internal surface of the drive sleeve 30. The guideposts 24 of the piston rod 20 are adapted to work within the helical groove 38 of drive member 30.

A first end of the first flange 32 is adapted to conform to a second side of the insert 16. A part nut 40 is located between the drive sleeve 30 and the main housing 2, disposed between the first flange 32 and the second flange 34. In the illustrated arrangement, the part nut 40 comprises a half-nut. The part nut 40 has an internal helical groove matching the intermediate helical groove 38 of the drive sleeve 30. In one preferred arrangement, the outer surface of the part nut 40 and an internal surface of the main housing 4 are keyed together by way of splines 6 to prevent relative rotation between the part nut 40 and the main housing 4, while allowing relative longitudinal in movement between these two components.

A dose dial sleeve 70 is provided outside of drive member 30 and clutch 60 and radially inward of the main housing 4. Towards the second end 64 of the clutch means 60 there is located a radially inwardly directed flange 62. The dose dial sleeve 70 comprises a distal end and a proximal end. A helical groove 74 is provided about an outer surface 72 of the dose dial sleeve 70. The main housing 4 is provided with a window 44 through which a part of an outer surface 72 of the dose dial sleeve 70 may be viewed. The main housing 4 is further provided with a helical rib 46, adapted to be seated in the helical groove 74 on the outer surface of the dose dial sleeve 70. In one preferred arrangement, the helical rib 46 extends for a single sweep of the inner surface of the main housing 4.

Returning to FIGS. 1-2, a dose dial grip 76 is disposed about an outer surface of the second end of the dose dial sleeve 70. An outer diameter of the dose dial grip 76 preferably corresponds to the outer diameter of the main housing 4. The dose dial grip 76 is secured to the dose dial sleeve 70 to prevent relative movement between these two components. An annular recess 80 located in the second end of the dose dial grip 76 extends around the opening 78. A button 82 of generally "T" section is provided at a second end of the device.

To dial a dose in the arrangement illustrated in FIGS. 1-2, a user holds the main housing 4 in his or her left hand and uses the right hand to rotate the dose dial grip 76 in a direction away from the user. With the clutch 60 engaged, the drive sleeve 30, the clutch 60 and the dose dial sleeve 70 rotate with the dose dial grip 76 towards the user. Audible and tactile feedback of the dose being dialed is provided by a clicker and the clutch 60. The helical groove 74 on the dose dial sleeve 70 and the helical groove 38 in the drive sleeve 30 have the same lead. This allows the dose dial sleeve 70 to extend in a proximal direction away from the main housing 4 (See FIG. 2). In this manner, the drive sleeve 30 climbs the piston rod 20 at the same rate. Rotation of the piston rod 20 is prevented due to the opposing directions of the overhauled and driven threads on the piston rod 20. The part nut 40, keyed to the main housing 4, is advanced along the intermediate thread 36 by the rotation of the drive sleeve 30.

A visual indication of the dose that may be dialed, for example reference numerals or a scale, may be provided on the outer surface 72 of the dose dial sleeve 70 and viewed through window 44.

Should a user inadvertently dial beyond a desired dosage, the drug delivery device allows the dosage to be dialed down without dispense of medicinal product from the cartridge. In order for the user to dial down the dosage, the dose dial sleeve 70 is rotated in a direction towards the user and the dose dial grip 76 is counter rotated. This causes the system to act in reverse. When the desired dose has been dialed, the user may then dispense this dose by depressing the button 82. As the user depresses the button 82, this displaces the clutch 60 axially with respect to the dose dial sleeve 70. However the clutch 60 remains keyed in rotation to the drive sleeve 30. The dose dial sleeve 70 and associated dose dial grip 76 are now free to rotate (guided by the helical rib 46 located in helical groove 74).

The drive sleeve 30 is prevented from rotating with respect to the main housing 4 though it is still free to move axially with respect thereto. The longitudinal axial movement of the drive sleeve 38 causes the piston rod 20 to rotate through the opening 18 in the insert 16, thereby to advance the piston 10 in the cartridge 8.

Exemplary embodiments of the present drug delivery device have been described. Those skilled in the art will understand, however, that changes and modifications may be made to these embodiments without departing from the true scope and spirit of the presently proposed drug delivery device, which is defined by the claims. In particular, the improved piston rod of our invention can be used in a number of varying and different drug delivery device designs.

The invention claimed is:

1. A piston rod for a device, especially a pen-type injector, comprising an elongated member having a distal end and a proximal end where the proximal end has at least two sets of guideposts, where at least one set has at least two guideposts that are in axial alignment with each other and are configured for transmitting axial and rotational forces from a drive member having at least one internal groove with a pitch P, wherein each guidepost is configured as a post, peg, or pin having a single longitudinal axis projecting radially outward from the proximal end and the at least two sets of guideposts are located on opposing sides of the proximal end of the piston rod.

2. The piston rod of claim 1 where the guideposts have circular or oblong shapes.

3. The piston rod of claim 1 where the guideposts are separated by a distance equal to pitch P.

4. The piston rod of claim 1 further characterized in that each set of guideposts has three guideposts that are separated by a distance equal to pitch P.

5. A piston rod for a pen device, especially a pen-type injector, comprising an elongated member having a distal end and a proximal end where the proximal end has at least two sets of two or more guideposts, where the guideposts are in axial alignment with each other and are configured for transmitting axial and rotational forces from a drive member having at least one internal groove with a pitch P, wherein each guidepost is configured as a post, peg, or pin having a single longitudinal axis projecting radially outward from the proximal end and the at least two sets of guideposts are located on opposing sides of the proximal end of the piston rod.

6. A drug delivery device, said device comprising:
    a drug delivery device housing;
    a retaining means for a medicament contained in said drug delivery device housing;
    a drive mechanism; and
    a piston rod in communication with at least one groove in the drive mechanism comprising an elongated member having a distal end and a proximal end, where the proximal end has at least two sets of two or more guideposts extending outwardly from the elongated member and is configured to engage a corresponding groove in a drive member and for transmitting axial or rotational forces from the drive member, wherein at least one of the at least two sets of two or more guideposts have guideposts configured as a post, peg, or pin having a single longitudinal axis projecting radially outward from the proximal end and the at least two sets of guideposts are located on opposing sides of the proximal end of the piston rod.

7. A pen type drug delivery device, said device comprising:
    a drug delivery device housing, said housing having a distal end for mounting a needle assembly and a proximal end comprising a dose dial grip;
    a cartridge contained in said housing, said cartridge containing a medication;
    a drive mechanism; and
    a piston rod in communication with at least one groove in the drive mechanism comprising an elongated member having a distal end and a proximal end, where the proximal end has at least two sets of two or more guideposts extending outwardly from the elongated member and is configured to engage a corresponding groove in a drive member and for transmitting axial or rotational forces from the drive member, wherein each guidepost is configured as a post, peg, or pin having a single longitudinal axis projecting radially outward from the proximal end and the at least two sets of guideposts are located on opposing sides of the proximal end of the piston rod.

* * * * *